(12) United States Patent
Poole

(10) Patent No.: US 6,666,820 B1
(45) Date of Patent: Dec. 23, 2003

(54) MATHEMATICAL THERAPEUTIC OUTCOMES MODEL FOR PREDICTING CLINICAL EFFICACY THERAPIES

(76) Inventor: Michael D. Poole, 6431 Fannin St., Suite 6-132, Houston, TX (US) 77030

( * ) Notice: Subject to any disclaimer, the term of this patent is extended or adjusted under 35 U.S.C. 154(b) by 201 days.

(21) Appl. No.: 09/995,903

(22) Filed: Nov. 28, 2001

Related U.S. Application Data

(60) Provisional application No. 60/253,535, filed on Nov. 28, 2000.

(51) Int. Cl.$^7$ ................................................. A61B 5/00
(52) U.S. Cl. ........................ 600/300; 128/920; 128/897
(58) Field of Search ................................. 600/300–301; 128/920–925, 897–898; 705/2–4; 702/19; 706/924

(56) References Cited

U.S. PATENT DOCUMENTS 6,520,917 B1 * 2/2003 Kunig et al. ................ 600/481

OTHER PUBLICATIONS

Sinus and Allergy Health Partnership, "Antimicrobial Treatment Guidelines for Acute Bacterial Rhinosinusitis," Otolaryngol Head Neck Surg. Jul. 2000; 123 No. 1, Part 2, (Suppl.): ppS1–S31, and particularly pp. S5–S31.

* cited by examiner

Primary Examiner—Max F. Hindenburg
Assistant Examiner—Michael Astorino
(74) Attorney, Agent, or Firm—Bracewell & Patterson, L.L.P.

(57) ABSTRACT

A method and system allow a physician or other clinical care provider to consistently and logically place and correlate the various interdependent facts or assumptions made during the examination and testing of a patient in a fashion that provides a numerical estimate of treatment effectiveness. The primary and secondary factors are gathered and input to the system, and each factor may have a numerical effect on another factor in the calculation. The system guides the clinician in the selection of a treatment protocol from the available treatment regimes.

11 Claims, 3 Drawing Sheets

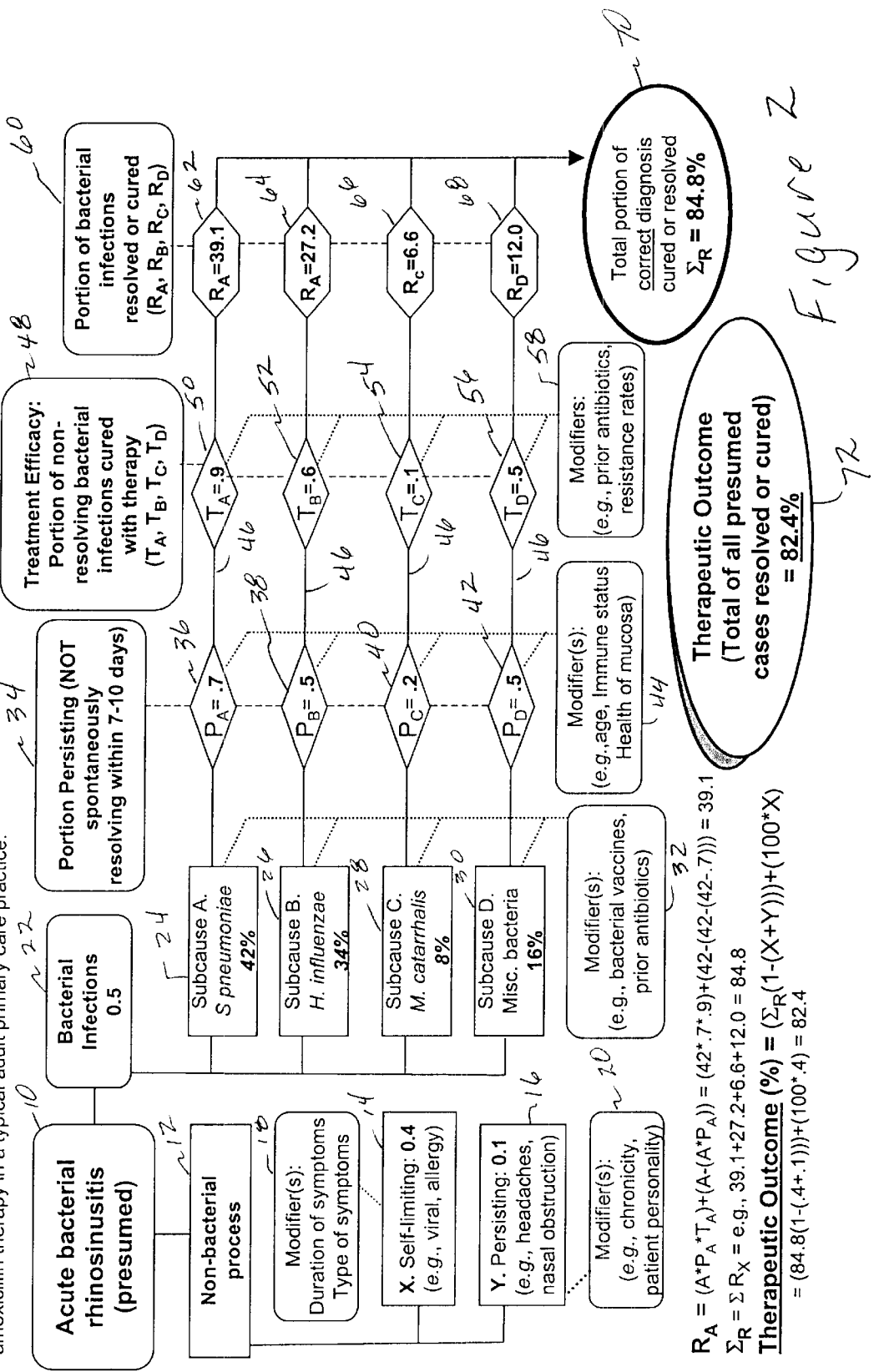

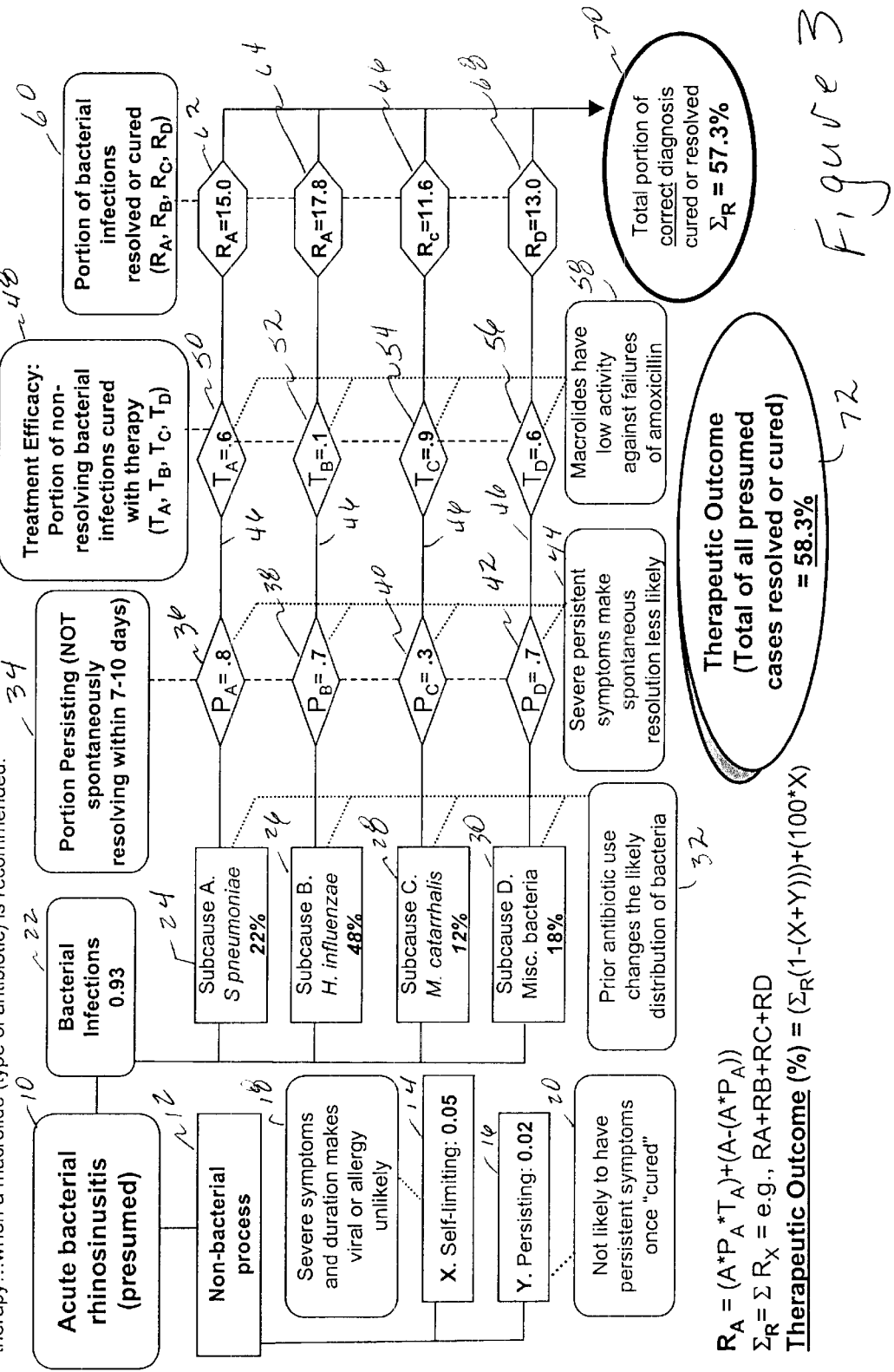

MATHEMATICAL THERAPEUTIC OUTCOMES MODEL FOR PREDICTING CLINICAL EFFICACY THERAPIES

This application claims the benefit of U.S. Provisional Patent Application Ser. No. 60/253,535, filed Nov. 28, 2000.

BACKGROUND OF THE INVENTION

1. Field of the Invention

The present invention relates generally to the field of methods and systems for aiding clinical health care providers in choosing the most appropriate therapy for a given clinical situation and predicting the effectiveness of a prescribed course of action in treating disease.

2. Description of the Prior Art

Traditionally, a medical practitioner has applied clinical findings and circumstances, along with his experience, knowledge, and training, to predict the effectiveness of one course of treatment over another. Such a prediction has assisted the health care provider in choosing the most appropriate therapy for a given clinical situation. In many cases, the clinician has used subconscious decision-making algorithms. Given the relatively large number of variables and factors that can be involved in making even the simplest medical decisions, it is possible that certain factors or considerations may not always be given the proper weight in determining the most effective treatment for a specific clinical condition or disease.

In recent years, computers have been adapted in a variety of ways to assist clinicians in determining a course of treatment for their patients. For example, in U.S. Pat. No. 6,081,786, titled Systems, Method and Computer Program Products For Guiding The Selection of Therapeutic Treatment Regimens, Barry et al. taught a way to guide a health care provider in the selection of a therapeutic treatment regimen for a known disease, such as HIV. The method included providing patient information to a computer, generating a ranked listing of therapeutic treatment regimens, and generating information for one or more treatment regimens in the listing based on patient information and expert rules. The computer used three knowledge bases, including different therapeutic treatment regimens, expert rules, and advisory information useful for the treatment of a patient with different constituents of the different therapeutic treatment regimens.

Similarly, in U.S. Pat. No. 6,126,596, titled Apparatus and Method For Evaluating a Client's Condition and The Concordance of a Clinician's Treatment With Treatment Guidelines, Freedman taught a system to collect data directly from a patient and use this data to diagnose and to establish the severity of a client's condition. The system used this data to look up one or more appropriate treatments according to treatment guidelines stored in its memory. The system then used this information to monitor if the treatment decisions made by the treating clinician or other medical provider was consistent with the stored treatment guidelines.

Many such systems have been proposed which attempt to harness the vast analysis capability of a computer, and to exploit the computer's speed in taking into account a large number of variables. Unfortunately, none of the systems thus far proposed utilize a dynamic system to predict the effectiveness of a proposed treatment protocol, in order to assist the clinician in selecting the most effective course of treatment for a patient. The present invention is directed to this shortfall in the art.

SUMMARY OF THE INVENTION

The present invention provides a method and system which allows a user, such as a physician or other clinical care provider, to consistently and logically place and correlate the various interdependent facts or assumptions made during the examination and testing of a patient in a fashion that provides a numerical estimate of treatment effectiveness.

When a patient or other person presents with an unknown disease or condition, a physician or other care giver typically conducts a physical examination of the patient, which may include certain laboratory or other tests, as well as an interview, in an attempt to ascertain the nature of the patient's problems. After conducting an examination and interview, the physician typically possesses certain facts which bear on his or her determination of the patient's disease. Through the use of appropriate algorithms and/or formulas, certain facts from a particular case may be used to produce and describe the efficacy of a specific treatment modality for a particular disease or ailment.

For instance, in the case of bacterial rhinosinusitis, certain variables are known to effect the outcome of various types of treatment. Typically, bacterial rhinosinusitis is treated with antibiotics. However, in some cases, the disease may spontaneously resolve or may not resolve even after a course of antibiotics, such as in the case where the cause of the sinusitis is viral rather than bacterial. In practicing the present invention, the physician provides the system with the required data which corresponds to the variables identified for the given disease or condition which is being considered. The system of the invention then processes these variables using certain predetermined algorithms to generate a probability of effectiveness. These indicators correspond to the efficacy of various treatment options to aid the physician in selecting an appropriate option for a particular patient.

Thus, in specific aspect, the present invention provides a method of predicting the efficacy of a medical treatment. More particularly, that method comprises the steps of developing a clinical diagnosis of a disease; determining the statistical incidence of incorrect diagnosis of the disease; determining the statistical incidence of the contribution of known pathogens to the correctly diagnosed disease; determining the statistical incidence of disease caused the determined pathogens, which does not spontaneously resolve; determining the statistical efficacy of predetermined treatments for the incidence of the determined disease; and based on these determinations, calculating the likelihood of resolution of the disease, indicative of the efficacy of the predetermined treatments. The present invention further provides a means of carrying out this method.

The present invention also provides a method and a system which comprises an interdependent array of data, wherein alteration of any entry in the array of data alters the end results of the prediction of the efficacy of the treatment. The array of data comprises the clinical picture of the patient having the presumed diagnosis, as well as the enumerated factors which alter that clinical picture.

The system and method of the present invention may be employed in a number of embodiments. For instance, it may be used as part of a spreadsheet which may be used in conjunction with any conventional personal computer or similar computer device. It may be employed as a stand alone or self contained computer application or applet or it may be used in conjunction with a suitable database program.

These and other features and advantages of the present invention will be apparent to those skilled in the art of computer aided medical treatment systems from a review of the following detailed description along with the accompanying drawing figures.

BRIEF DESCRIPTION OF THE DRAWINGS

FIG. 2 is a logic flow diagram of the routine of FIG. 1 with a specific example of a condition of a patient showing the effects of the variables which alter the ultimate outcome of the prediction of the effectiveness of a prescribed course of action.

FIG. 3 is a logic flow diagram of routine of FIG. 2, illustrating the effects of various modifiers on the outcome.

DETAILED DESCRIPTION OF THE PREFERRED EMBODIMENTS

Figure 1:
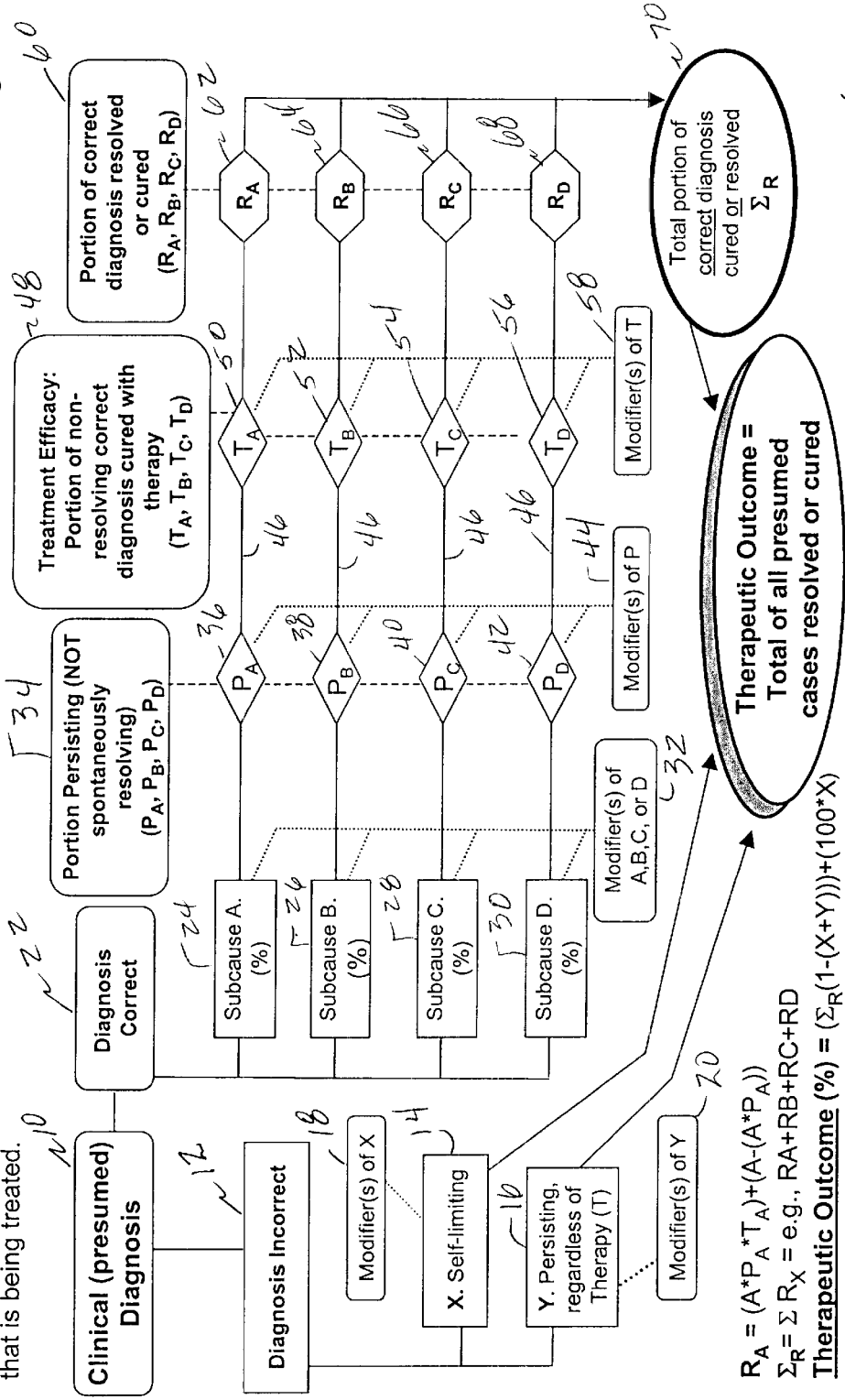
FIG. 1 is a logic flow diagram of a routine adapted to carry out the present invention.

The present invention provides a system and method for providing a physician or other care giver a probability of cure of various treatment methods or modalities for a specific disease or diagnosis. Typically, a physician obtains certain clinical information from a patient during an examination and interview. Such information may include, for instance, the type and duration of any symptoms the patient has or is experiencing, certain physical data relating to the patient, such as temperature, blood pressure, and the like and the results of any laboratory tests that were conducted. From this information, the physician typically ascertains likely causes for the various symptoms and data collected. Once a likely cause has been determined, the physician must choose an appropriate therapy or treatment for the disease. Given the myriad of treatments available today, such as numerous antibiotics in the case of bacterial diseases, and the fact that many diseases may respond differently to a given drug depending on the specific patient (i.e., depending on the patient's tolerance and prior use of a given drug or interactions between a particular drug and other drugs a patient may be taking), the present system provides a numerical estimate of treatment effectiveness which would be useful to a physician in evaluating possible therapies.

In a preferred embodiment of the invention, the present system and method may be used to assess the efficacy of various antibiotics in treating bacterial sinusitis, for example. Initially, a first, specific group or set of primary variables is determined. Such variables may include any suitable factors or determinants. For instance, the false positive diagnosis rate should first be determined. In the case of bacterial sinusitis, the false positive rate may be further split or subdivided into two categories: (a) cases where the symptoms or disease have historically spontaneously resolved; and (b) cases where the symptoms or disease did not spontaneously resolve. Typically, an antibiotic is ineffective in treating patients where the initial diagnosis was bacterial infection, but the patient actually suffers from a viral infection. Therefore, the condition would resolve spontaneously, regardless of antibiotic usage. In other false positive cases, the disease may not resolve spontaneously, with or without the use of antibiotics. For example, a chronic migraine headache may all too commonly be misdiagnosed as a sinus infection. Alternatively, the first step of the present invention may simply involve determining the percentage of cases presenting a specific clinical condition which are accurately diagnosed.

In the second step of the invention, the prevalence or percentage of various "subcauses" or specific agents is determined. In the case of bacterial sinusitis, there are various species of bacteria that account for most cases. These are *Streptococcus pneumoniae, Hemophilus influenzae,* and *Moraxella catarrhalis,* and miscellaneous bacteria. Through clinical research, the relative prevalence of each of these pathogens as the cause of sinusitis has been determined or can be estimated.

In the third step, the spontaneous resolution rate for each of the subcauses is estimated. Each of the bacteria identified as causing sinusitis have varying rates of spontaneous cure or resolution. Therefore, even a poor antibiotic may appear to work well if it were used in cases where the disease spontaneously resolved.

The fourth and most important variable in the case of bacterial sinusitis is the effectiveness of each treatment against each subcause (type of bacteria). Clinical research data, including antibiotic surveillance data, help determine the appropriate value for any given antibiotic.

The following table demonstrates the variables for a typical practice:

| Subcause | Prevalence | Spontaneous Resolution Rate | Effectiveness of Antibiotic X |
| --- | --- | --- | --- |
| S. pneumoniae | 45% | 30% | 90% |
| H. influenzae | 25% | 50% | 55% |
| M. catarrhalis | 12% | 80% | 5% |
| Miscellaneous | 18% | 50% | 50% |

False Positive Diagnosis, Spontaneously Resolving Rate: 40%

False Positive Diagnosis, Non-resolving Rate: 5%

While the primary variables can provide an acceptable model for providing a numerical indicator of treatment effectiveness, the inclusion of additional, secondary variables can provide greater accuracy. Such secondary variables can include any factors which impact the primary variables. For instance, a number of variables may effect the spontaneous resolution rate. Where a physician chooses to treat a patient with antibiotics when the sinus symptoms have been present for only five days, as opposed to the recommended 7–14 days, the likelihood that the physician is actually treating a viral process goes up. However, certain symptoms, such as tenderness upon tapping the sinus or visible pus may decrease the false positive rate and make diagnosis of bacterial infection more likely.

Secondary variables that affect the types of distribution of the subcauses may also be included. For instance, if a patient has been vaccinated against one of the bacterial causes, the expected prevalence of that organism would be deceased. Prior antibiotic therapy would typically be more effective against some subcauses than others.

Additional secondary variables may also include those that affect the resolution rates of the subcauses, such as in the case of immunocompromised patients, the elderly or the very young. These patients typically do not clear infections as easily or as consistently as others.

Finally, in the case of bacterial sinusitis, secondary variables that affect the efficacy of an antibiotic against the various subcauses may be included. For example, if a patient has received an antibiotic recently, not only are the bacteria that are causing the current episode of sinusitis more likely to be resistant to that class of antibiotics, but they are also more likely to be resistant to other classes of antibiotics. Poor compliance or reduced absorption (such as due to diarrhea, for instance) might also reduce antibiotic effectiveness.

Once the appropriate primary and secondary variables have been identified or determined, a number of formulas or algorithms may be used to produce the desired numerical estimate of treatment effectiveness. In the case of bacterial sinusitis, for instance, the following formulas may be used to generate an estimate:

> Persisting rate for each subcause=(1−spontaneous resolution rate)
>
> Spontaneously cured infections for each subcause=(Prevalence*(1−persisting rate))
>
> Bacteriologic cure rate for each subcause=(Prevalence*Persisting rate*Efficacy of Antibiotic)+Spontaneously cured rate
>
> Total cure rate=Sum of all subcause cure rates
>
> Overall clinical cure rate=Total cure rate+False positive resolving rate Each of the formulas may be solved using variables previously identified and culminating in a determination of the clinical efficacy, expressed here as the overall clinical cure rate, of a specific antibiotic to a set of bacteria known to cause bacterial sinusitis. It should be understood by those skilled in the art that the system of the present invention could be modified to generate efficacy data for any number of diseases, conditions or ailments by identifying the pertinent variables and applying those variables to a suitable set of algorithms or formulas.

Now that the invention has been introduced, consider FIG. 1. As previously described, a physician or other clinician typically interviews a patient, and along with certain test results arrives at a clinical diagnosis 10. The remainder of the logic flow of FIG. 1 is directed to a well defined methodology of predicting the probability of a cure of the patient. Since many maladies present the same or similar symptoms, even the most skilled clinician will arrive at a diagnosis which is incorrect, which is illustrated in FIG. 1 as step 12. Further, the rate of misdiagnosis may be established with some degree of accuracy from historical treatment of patients with the same presentation. This is one of the "primary variables" of the present invention.

Of those cases which are misdiagnosed, some cases are spontaneously resolved, represented in FIG. 1 as step 14, and the rate of self-limiting or spontaneously resolving misdiagnosed disease is designated as X in the algorithm. The remainder of the misdiagnosed cases, shown as step 16, do not spontaneously resolve, and persist despite the treatment of the physician. This factor is designated as Y. Each of the factors of spontaneous resolution, X, and non-spontaneous resolution, Y, may be altered by other influences, shown in FIG. 1 as modifiers of X, shown as step 18, and modifiers of Y, shown as step 20. For example, if a patient is diagnosed with a bacterial infection, and is actually suffering from a viral infection, the value of X may be modified by such factors as the patient's general health, the quantity and quality of the patient's diet including in the ingestion of multivitamins, and so on. Note also that for a constant value of step 12, then a change in the value of X has a direct and inverse effect on the value of Y.

Step 22 is the result of the number of correctly diagnosed maladies among the patient population. As previously described, the diagnosis may be bacterial sinusitis. There are primarily three main bacterial strains which are known to cause bacterial sinusitis, and a miscellaneous category. These subcauses of bacterial sinusitis are shown in FIG. 1 as steps 24, 26, 28, and 30, respectively. Each of the subcauses has a known or determinable prevalence in the causation of the disease, expressed in FIG. 1 as a percentage. Further, other factors may cause one pathogen to be more prevalent than historically indicated, as shown in FIG. 1 as step 32, wherein the values within the steps are modified.

In step 34, the rate of persistent disease, wherein the disease is not spontaneously resolved, is factored into the equation. This factor thus includes in the calculation of likely cure of the disease the rate at which a patient will likely be cured, no matter what the treatment. And the rate-of spontaneous (or non-spontaneous) resolution is different for each pathogen, as shown by steps 36, 38, 40, and 42, and designated by $P_A$, $P_B$, $P_C$, and $P_D$ in FIG. 1. Further, the rate of non-spontaneous resolution is effected by additional factors, as indicated by step 44.

Thus, a set of lines 46 represent a rate of correctly diagnosed disease which will not spontaneously resolve, and a separated out into a number of predetermined subcauses. These lines represent patients who will then benefit from a properly selected course of treatment. In step 48, the portion of non-resolving correct diagnosis which is cured with therapy is factored in. As shown in steps 50, 52, 54, and 56, the efficacy of the available treatments is different, depending on the subcause of the disease, The treatment efficacy is designated as $T_A$, $T_B$, $T_C$, and, $T_D$ is FIG. 1, and each rate of efficacy is also modified by other factors, as shown in step 58.

The cure rate for each subcause is therefore determined in step 60, that is the portion of the correct diagnosis which is resolved or cured, and shown for each subcause as $R_A$, $R_B$, $R_C$, and $R_D$, respectively. The value of $R_A$ is given by $(A*P_A*T_A)+(A-(A*P_A))$. $R_B$, $R_C$, and $R_D$ are calculated in a similar fashion. These portions are then summed in step 70, to provide the total portion of those correctly diagnosed which are cured or resolved, shown as $\Sigma_R$ in FIG. 1. $\Sigma_R$ is given by $\Sigma R_X$, that is $R_A-R_B+R_C+R_D$. Step 72 then provides the end result, the Therapeutic Outcome. The therapeutic outcome is the total of all presumed cases resolved or cured, regardless of the accuracy of the diagnosis or the efficacy of the treatment, although both are major contributing factors. The therapeutic outcome is given by a percentage value equal to $(\Sigma_R(1-(X+Y)))+(100*X)$.

The system of the present invention can be implemented using any suitable technology. For example, the system may be constructed or programmed into a spreadsheet application wherein the user supplies certain data and the necessary formulas or algorithms as herein described use the supplied data to calculate treatment efficacy. Similarly, the system may be employed as a self-contained computer application or applet. Rather than entering data into a spreadsheet, the user may be presented with graphic data choice boxes or buttons, such as drop-down menus, slider bars or "radio buttons" which are commonly used in Internet or world wide web-based applications. These data choice mechanisms allow the user to choose the desired value for each of the required variables. The system may then provide the user with certain feedback based on the formulas which have been incorporated or programmed into the system. Any suitable programming language and any suitable platform may be used with the present system. A database system may also be used in conjunction with the system of the present invention. The values for the required variables may be collected from multiple patients, for instance, and a typical or mean value used in the various formulas.

Turning now to FIG. 2, a specific example of the present invention as illustrated and described in respect of FIG. 1 is provided. The same elements in FIGS. 1 and 2 are numbered the same. In the example depicted in FIG. 2, the presumed clinical diagnosis is acute bacterial rhinosinusitis. If the patient is actually suffering from a non-bacterial process, then step 12 applies. Statistics show that 40% of patients that present symptoms of acute bacterial rhinosinusitis, although incorrectly diagnosed, will spontaneously resolve, as shown in step 14. This statistical number, however, is modified by the modifiers of step 18, including the length of time that the patient has been experiencing the symptoms, the types of symptoms, etc. Similarly, step 16 illustrates that 10% of the patients presenting the same symptoms will not benefit from the treatment of an acute bacterial rhinosinusitis, and thus their symptoms will persist. This statistical number is modified by the chronicity of the development of the disease, the personality of the patient, etc.

Those patients who are correctly diagnosed with acute bacterial rhinosinusitis represent 50 of those presenting the symptoms. Of those, 42% of the cases are caused by *A. pneumoniae*, as shown in step 24, and so on for the other subcauses. Continuing through the logic flow, step 36 illustrates that 70% of those cases as a result of that subcause will not spontaneously resolve with a 7–10 day period, and step 50 shows that the appropriate therapy is 90% effective in curing the disease. These factors result in a resolution $R_A$ of 39.1. Further, the sum of all resolutions for the various subcauses results in $\Sigma_R$ of 84.8% and a therapeutic outcome of 82.4%, when taking into account the incorrectly diagnosed patients.

As previously described, each of the factors may be modified by the clinical picture actually presented by a specific patient. Such a case is illustrated in FIG. 3. Historical factors and clinical findings are variable that modify the values of the major variables. As opposed to the "average" values shown and described in FIG. 2, the situation presented in FIG. 3, as an example, might reflect a patient with an extended period of server unilaterial sino-nasal symptoms, no perior history of facial pain or headaches, and a history of failed amoxicillin therapy, when a specific type of antibiotic is recommended. The severity and the duration of the symptoms indicates to the system that it is less likely that the patient is actually suffering from an allergy or that the cause of the symptoms is viral, as indicated by the modifiers of step 18. These facts also alter the values of X and Y. These factors in the clinical evaluation picture also mean that the diagnosis of acute bacterial rhinusitis is far more certain, as shown in step 22. The prior antibiotic use, although unsuccessful, changes the likely distribution of bacteria as the source of the disease, a modifier of step 32 which changes the fractional distribution of steps 24, 26, 28, and 30. The severe persistent symptoms make spontaneous resolution less likely, as shown in step 44, and the previous failure of amoxicillin means that the likelihood of efficacy of the indicated antibiotic, a macrolide, is reduced. All of the factors combined results in a predicted therapeutic outcome in the example of FIG. 3 of 58.3%, substantially lower than the 82.4% using the average numbers of FIG. 2.

The principles, preferred embodiment, and mode of operation of the present invention have been described in the foregoing specification. This invention is not to be construed as limited to the particular forms disclosed, since these are regarded as illustrative rather than restrictive. Moreover, variations and changes may be made by those skilled in the art without departing from the spirit of the invention.

I claim:

1. A method of predicting the efficacy of a medical treatment of a patient, comprising the steps of:
   a. developing a clinical diagnosis of a disease;
   b. determining the statistical incidence of incorrect diagnosis of the disease;
   c. determining the statistical incidence of the contribution of known pathogens to the correctly diagnosed disease;
   d. determining the statistical incidence of disease, caused by the pathogens determined in step 1.c, which does not spontaneously resolve;
   e. determining the statistical efficacy of predetermined treatments for the incidence of disease determined in step 1.d; and
   f. based on the determinations of steps 1.a through 1.e, calculating the likelihood of resolution of the disease, indicative of the efficacy of the predetermined treatments.

2. The method of claim 1, further comprising the step of, after the step of determining the statistical incidence of incorrect diagnosis of the disease, then determining the statistical incidence of those cases of incorrect diagnosis which will spontaneously resolve.

3. The method of claim 2, further comprising the step of, after the step of determining the statistical incidence of those cases of incorrect diagnosis which will spontaneously resolve, then modifying the determined statistical incidence of those cases of incorrect diagnosis which will spontaneously resolve by a modifier, the modifier based on factors determined from the clinical picture of the patient.

4. The method of claim 1, further comprising the step of, after the step of determining the statistical incidence of incorrect diagnosis of the disease, then determining the statistical incidence of those cases of incorrect diagnosis which will not spontaneously resolve.

5. The method of claim 4, further comprising the step of, after the step of determining the statistical incidence of those cases of incorrect diagnosis which will not spontaneously resolve, then modifying the determined statistical incidence of those cases of incorrect diagnosis which will not spontaneously resolve by a modifier, the modifier based on factors determined from the clinical picture of the patient.

6. The method of claim 1, further comprising the step of, after the step of determining the statistical incidence of the contribution of known pathogens to the correctly diagnosed disease, modifying the statistical incidence of the contribution of each of the known pathogens to the correctly diagnosed disease by a modifier, the modifier based on factors determined from the clinical picture of the patient.

7. The method of claim 1, further comprising the step of, after the step of determining the statistical incidence of disease, caused by the pathogens determined in step 1.c, which does not spontaneously resolve, modifying the statistical incidence of disease, caused by the pathogens determined in step 1.c, which does not spontaneously resolve by a modifier, the modifier based on factors determined from the clinical picture of the patient.

8. The method of claim 1, further comprising the step of, after the step of determining the statistical efficacy of predetermined treatments for the incidence of disease determined in step 1.d, modifying the statistical efficacy of predetermined treatments for the incidence of disease determined in step 1.d by a modifier, the modifier based on factors determined from the clinical picture of the patient.

9. A system for predicting the efficacy of a medical treatment of a patient, the system comprising:
   a. means for developing a clinical diagnosis of a disease;
   b. means for determining the statistical incidence of incorrect diagnosis of the disease;
   c. means for determining the statistical incidence of the contribution of known pathogens to the correctly diagnosed disease;
   d. means for determining the statistical incidence of disease, caused by the pathogens determined by means 9.c, which does not spontaneously resolve;
   e. means for determining the statistical efficacy of predetermined treatments for the incidence of disease determined by means 9.d; and f. means for calculating the likelihood of resolution of the disease, indicative of the efficacy of the predetermined treatments, based on the determinations of means 9.a through 9.e.

10. A method of predicting the efficacy of a medical treatment of a patient, comprising the steps of:
   a. assembling an interdependent array of data, the data comprising:
      i. a clinical diagnosis of a disease;
      ii. statistical incidence of incorrect diagnosis of the disease;
      iii. statistical incidence of the contribution of known pathogens to the correctly diagnosed disease;
      iv. statistical incidence of disease, caused by the determined pathogens, which does not spontaneously resolve;
      V. statistical efficacy of predetermined treatments for the determined incidence of disease; and
   b. based on the assembled data of step 10.a, calculating the likelihood of resolution of the disease, indicative of the efficacy of the predetermined treatments.

11. The method of claim 10, wherein the alteration of any of the interdependent array of data alters the indication of the efficacy of the predetermined treatments.

* * * * *

UNITED STATES PATENT AND TRADEMARK OFFICE
CERTIFICATE OF CORRECTION

PATENT NO.      : 6,666,820 B1
DATED           : December 23, 2003
INVENTOR(S)     : Michael D. Poole It is certified that error appears in the above-identified patent and that said Letters Patent is hereby corrected as shown below:

<u>Title page, Item [54] and Column 1, lines 1-3,</u>
Title, delete "MATHEMATICAL THERAPEUTIC OUTCOMES MODEL FOR PREDICTING CLINICAL EFFICACY THERAPIES" and insert
-- MATHEMATICAL THERAPEUTIC OUTCOMES MODEL FOR PREDICTING CLINICAL EFFICACY OF THERAPIES --

Signed and Sealed this

Twenty-seventh Day of April, 2004

JON W. DUDAS
*Acting Director of the United States Patent and Trademark Office*